(12) United States Patent
Shin

(10) Patent No.: US 8,632,848 B2
(45) Date of Patent: Jan. 21, 2014

(54) SURFACE COATING METHOD FOR AN ORTHODONTIC CORRECTIVE BRACKET

(75) Inventor: Woo Seok Shin, Siheung-si (KR)

(73) Assignee: Hubit Co., Ltd., Gyeonggi-do (KR)

(*) Notice: Subject to any disclaimer, the term of this patent is extended or adjusted under 35 U.S.C. 154(b) by 0 days.

(21) Appl. No.: 13/388,053

(22) PCT Filed: Jul. 19, 2010

(86) PCT No.: PCT/KR2010/004683
§ 371 (c)(1),
(2), (4) Date: Jan. 30, 2012

(87) PCT Pub. No.: WO2011/019146
PCT Pub. Date: Feb. 17, 2011

(65) Prior Publication Data
US 2012/0128864 A1    May 24, 2012

(30) Foreign Application Priority Data
Aug. 10, 2009   (KR) .................. 10-2009-0073158

(51) Int. Cl.
B05D 3/10    (2006.01)
C23C 14/02   (2006.01)
C23C 14/18   (2006.01)
A61C 3/00    (2006.01)

(52) U.S. Cl.
USPC ............. 427/2.29; 427/523; 433/8; 433/10; 204/298.05; 204/298.41

(58) Field of Classification Search
USPC ............. 427/2.29, 523; 204/298.05, 298.41
See application file for complete search history.

(56) References Cited

U.S. PATENT DOCUMENTS

| | | | | |
|---|---|---|---|---|
| 4,197,175 A * | 4/1980 | Moll et al. | ............... | 204/192.38 |
| 4,364,731 A * | 12/1982 | Norling et al. | ............... | 433/218 |
| 4,636,285 A * | 1/1987 | Tarumoto et al. | ............. | 205/195 |
| 4,639,218 A * | 1/1987 | Jones et al. | ........................ | 433/8 |
| 5,037,522 A * | 8/1991 | Vergason | ................. | 204/298.41 |
| 6,299,438 B1 * | 10/2001 | Sahagian et al. | .................. | 433/6 |
| 2004/0063059 A1* | 4/2004 | Meckel | ............................. | 433/8 |

FOREIGN PATENT DOCUMENTS

| KR | 10-2000-0010119 A | 2/2000 |
|---|---|---|
| KR | 10-0647345 B1 | 11/2006 |
| KR | 20-2008-0005448 U | 11/2008 |

* cited by examiner

*Primary Examiner* — Cachet Sellman
(74) *Attorney, Agent, or Firm* — Rabin & Berdo, P.C.

(57) ABSTRACT

A surface coating method for an orthodontic corrective bracket is provided, in which each orthodontic bracket formed of ceramic is covered with a titanium coating layer having a predetermined thickness so as to be able to minimize a frictional force and to increase surface hardness and durability while a wire fitted into slots of the brackets applies orthodontic tension to teeth. Accordingly, when the teeth are corrected using the ceramic orthodontic brackets on whose surfaces the titanium coating layer having a predetermined thickness is formed, the frictional force can be minimized while the wire fitted into the slots of the brackets is applying the orthodontic tension to the teeth, and thus it is possible to realize a tooth movement path desired by an orthodontist and to shorten a treatment period.

2 Claims, 4 Drawing Sheets

SURFACE COATING METHOD FOR AN ORTHODONTIC CORRECTIVE BRACKET

CROSS-REFERENCE TO RELATED APPLICATION

This application claims priority to and the benefit of Korean Patent Application No. 10-2009-0073158, filed Aug. 10, 2009, the disclosure of which is incorporated herein by reference in its entirety.

BACKGROUND

1. Field of the Invention

The present invention relates to an orthodontic bracket, and more particularly, to a surface coating method for an orthodontic corrective bracket.

2. Discussion of Related Art

Orthodontics is a dental specialty and practice of preventing and correcting irregularities of the teeth, targeting abnormal tissues around teeth inducing bad arrangement of teeth, and includes correcting abnormalities of all teeth or occlusion, maxillary and mandibular prognathism, etc. called malocclusions.

Typical orthodontic methods are classified into a lingual side orthodontic method of attaching orthodontic brackets to the inside of the teeth so as to be adjacent to the tongue, and a labial side orthodontic method of attaching orthodontic brackets to the outside of the teeth so as to be adjacent to the lips. For cosmetic reasons, the lingual side orthodontic method has recently become more active. However, due to the limitations of a therapeutic effect and a percentage of orthodontic completion, the labial side orthodontic method is conducted fundamentally.

For reference, FIG. 1 illustrates a labial side orthodontic method of attaching orthodontic brackets 100 to the outside of the teeth so as to be adjacent to the lips.

As shown in a partial enlarged view of FIG. 1, the typical orthodontic brackets 100 may be fabricated in various shapes using metal, ceramic, resin, or the like. In the bracket of any shape, its back face 110 serves as an attachment face that is directly attached to a tooth, and an external face that is located on the opposite side of the back face 110 is provided with a slot 120 into which an orthodontic wire 200 interconnecting the brackets 100 is fitted.

To conduct the orthodontic treatment using these orthodontic brackets 100, an orthodontist applies an adhesive on predetermined parts of surfaces of teeth to be corrected, attaches the attachment faces 110 of the brackets 100 to the teeth surfaces to which the adhesive is applied before the adhesive is fully cured, aligns the brackets 100 so that the wire 200 is easily fitted into each slot 120, and waits until the adhesive is fully cured.

Afterwards, when the adhesive is fully cured, the orthodontist fits the wire 120 into the slots 120 formed in the external faces of the brackets 100 attached to the teeth, and fixedly supports opposite ends of the wire 200 with support members fixed to molars, thereby completing the installation of the orthodontic brackets 100.

Once the installation of the brackets 100 is completed, the wire 200 fitted into the slots 120 of the brackets 100 begins to apply orthodontic tension to the teeth.

As described above, while the wire 200 fitted into the slots 120 of the brackets 100 applies the orthodontic tension to the teeth, a frictional force acts on the brackets 100. Typically, the brackets 100 formed of metal have a relatively weaker frictional force with the wire 200 than the brackets 100 formed of ceramic or resin.

Thus, while the wire 200 fitted into the slots 120 of the brackets 100 formed of ceramic or resin applies the orthodontic tension to the teeth and thus displaces the teeth in a direction that is intended by the orthodontist, an excessive frictional force serves as an obstacle factor, so that a treatment period is prolonged more than needed, or pain or a treatment expense is increased. Further, while the wire 200 fitted into the slots 120 of the brackets 100 that are formed of ceramic or resin and are subjected to fatigue accumulation due to frictional resistance applies the orthodontic tension to the teeth, the surfaces of the brackets 100 that are formed of ceramic or resin are easily damaged by the frictional force, so that, during an orthodontic period, the damaged brackets 100 should be replaced, and thus the orthodontic treatment is delayed.

SUMMARY OF THE INVENTION

The present invention is directed to providing surface coating method for an orthodontic corrective bracket, in which each bracket formed of ceramic is covered with a titanium coating layer having a predetermined thickness so as to be able to minimize a frictional force and increase surface hardness and durability while a wire fitted into slots of the brackets applies orthodontic tension to teeth.

The present invention is also directed to providing surface coating method for an orthodontic corrective bracket, in which each bracket formed of ceramic is covered with a titanium coating layer having a thickness of 600 to 800 angstroms.

One aspect of the present invention provides surface coating method for an orthodontic corrective bracket that are formed of ceramic by grinding, sintering, injection molding, or pressing and are each configured so that a back face thereof serves as an attachment face that is directly attached to a tooth, whereas an external face thereof on an opposite side of the back face is provided with a slot into which an orthodontic wire interconnecting the orthodontic brackets is fitted. The method includes a first process of cleaning the orthodontic brackets to remove foreign materials from surfaces of the orthodontic brackets, and a second process of forming a titanium coating layer having a thickness of 600 to 800 angstroms on the surfaces of the ceramic orthodontic brackets from which the foreign materials are removed to reduce a frictional force with the orthodontic wire using an ion plating apparatus that generates an electron beam using a hollow cathode discharge (HCD) method to ionize titanium into deposition particles.

According to an embodiment of the present invention, the first process may include removing the foreign materials from the surfaces of the ceramic orthodontic brackets using an alkali detergent or an ultrasonic cleaner, cleaning the orthodontic brackets using water, finally removing the foreign materials from the surfaces of the orthodontic brackets using alcohol or acetone, and drying the orthodontic brackets.

According to another embodiment of the present invention, the second process may include: a first sub-process of fixing the plurality of orthodontic brackets for coating to a bracket holder that is installed in a chamber of the ion plating apparatus, receives a rotational force from a motor, and rotates at a predetermined angle, and loading titanium into a target electrode as a coating material; a second sub-process of operating a heater, which is installed in the chamber of the ion plating apparatus, for preheating within a temperature range from 200° C. to 300° C. for 30 to 50 minutes so as to allow the titanium coating layer to be readily formed on the surface of each orthodontic bracket, and changing a surface structure of each orthodontic bracket loaded in the chamber; a third sub-process of stopping the operation of the heater when the orthodontic brackets are preheated, cooling the orthodontic brackets for 3 to 5 minutes so as to maintain the changed surface structure of each orthodontic bracket, and operating a vacuum pump, which is installed on one side of the chamber to evacuate the inside of the chamber to a degree of vacuum of $1.0\times10^{-3}$ to $5.0\times10^{-3}$ torr required to form the titanium coating layer; a fourth sub-process of, when the inside of the chamber maintains the vacuum degree required to form the titanium coating layer, introducing argon (Ar) gas into the chamber via a plurality of gas inlets formed on one side of the chamber at 300 to 500 sccm for 4 to 10 minutes, applying power for generating an electron beam from an electron beam power supply to an electron gun for HCD and the target electrode, generating the electron beam resulting from glow discharge to ionize the Ar gas and to evaporate the titanium loaded on the target electrode into atomic or molecular particles, and generating plasma including Ar cations and evaporated titanium particles in the chamber; a fifth sub-process of, in a state where the plasma is generated in the chamber, introducing the Ar gas into the chamber for 5 to 10 minutes so as to allow the inside of the chamber to be maintained at a temperature of 1000° C. to 1500° C. while an amount of the Ar gas is being reduced, evaporating the titanium into the atomic or molecular particles, applying a voltage of 50 to 100 V of bias power for deposition from a bias power supply to the bracket holder at intervals of 30 to 60 seconds for 5 to 10 minutes, and forming the titanium coating layer having a thickness of 600 to 800 angstroms on the surfaces of the orthodontic brackets in order to reduce a frictional force with the orthodontic wire; and a sixth sub-process of, when the formation of the coating layer is completed, shutting off the electron beam generating power and the bias power, cooling the orthodontic brackets for 60 to 90 minutes, and unloading the orthodontic brackets from the chamber to terminate the coating operation when the temperature of the inside of the chamber is reduced to a temperature range of 50° C. to 80° C.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

Figure 1:
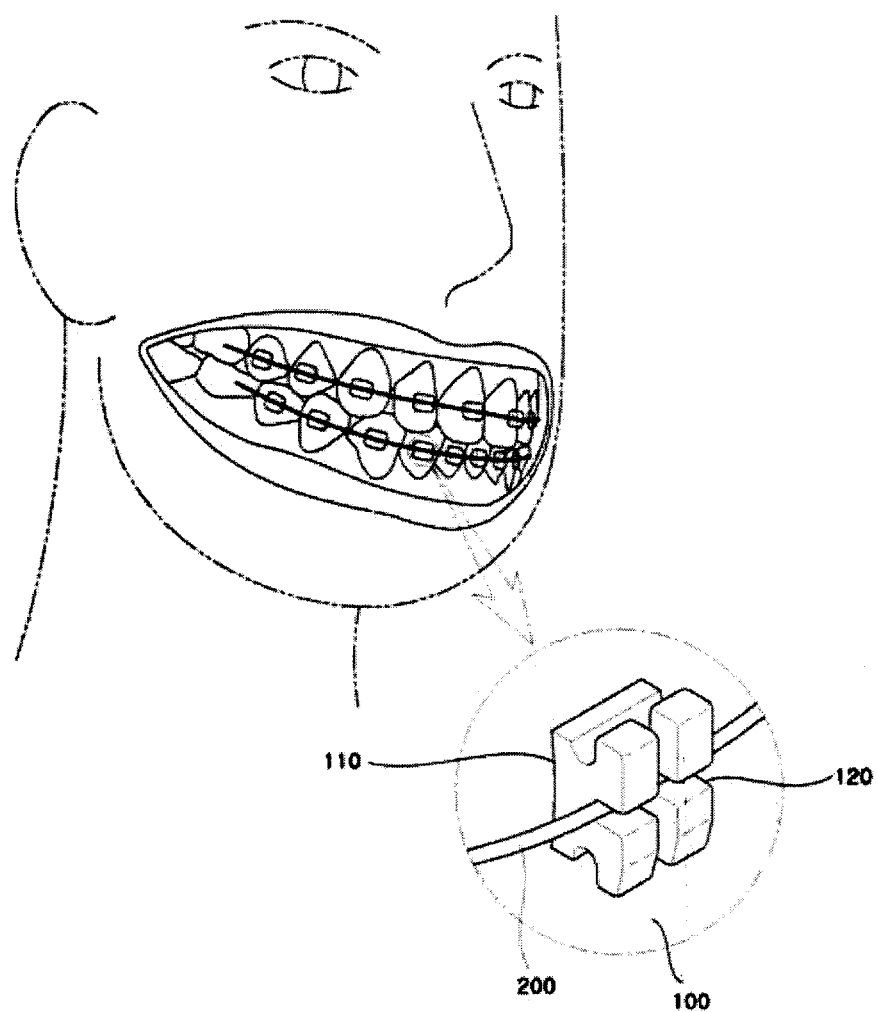
FIG. 1 illustrates a labial side orthodontic method of attaching orthodontic brackets to the outside of the teeth so as to be adjacent to the lips.

In a surface coating method for an orthodontic corrective bracket according to an exemplary embodiment of the present invention, the orthodontic brackets 100 are formed of ceramic by grinding, sintering, injection molding, or pressing. As shown in a partial enlarged view of FIG. 1, each orthodontic bracket 100 is configured so that a back face 110 thereof serves as an attachment face that is directly attached to a tooth, and an external face thereof on the opposite side of the back face 110 is provided with a slot 120 into which an orthodontic wire 200 interconnecting the brackets 100 is fitted.

Figure 2:
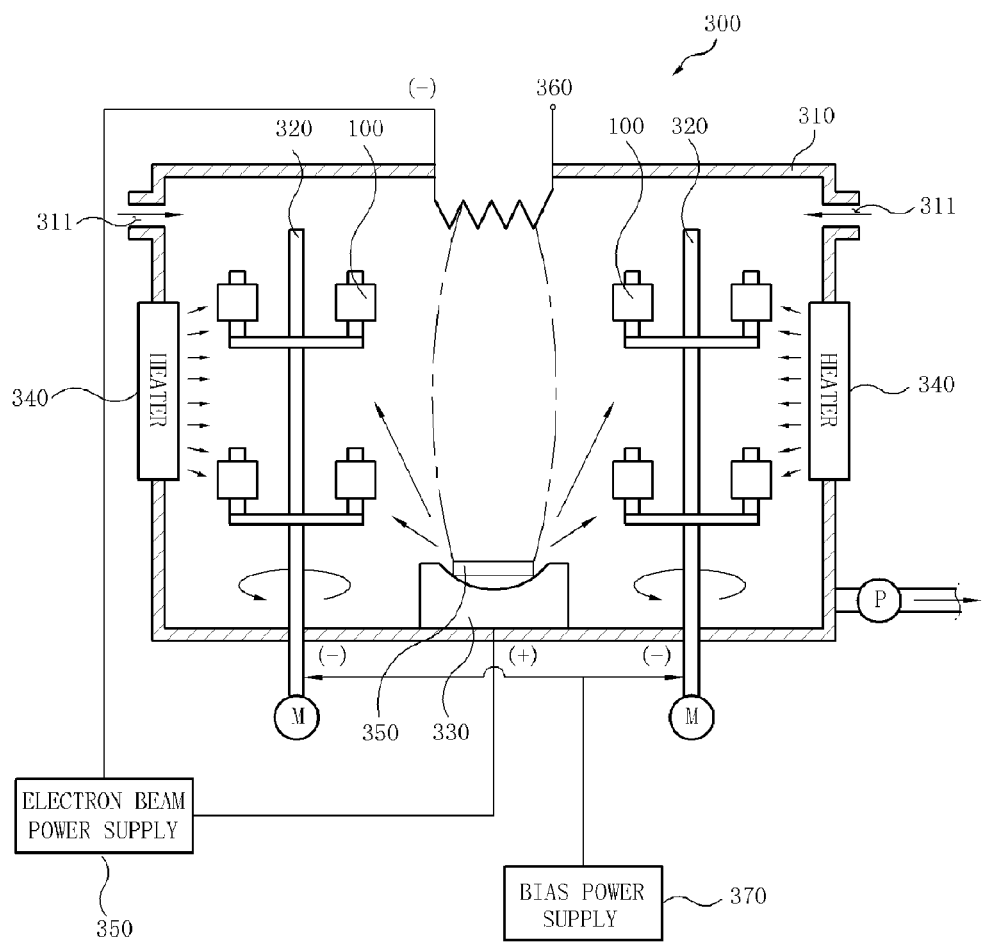
FIG. 2 illustrates configuration of an ion plating apparatus for performing a surface coating method for an orthodontic corrective bracket according to an exemplary embodiment of the present invention.

The surface coating method for an orthodontic corrective bracket according to an exemplary embodiment of the present invention is performed by an ion plating apparatus 300 that generates an electron beam using a hollow cathode discharge method and ionizes titanium into deposition particles, as shown in FIG. 2.

The ion plating apparatus 300 shown in FIG. 2 includes a chamber 310, a bracket holder 320, a target electrode 330, a heater 340, an electron beam power supply 350, an electron gun 360 for hollow cathode discharge (HCD), a bias power supply 370, a vacuum pump P, and a motor M.

The chamber 310 allows argon (Ar) gas to be introduced through a plurality of gas inlets 311 formed on one side thereof, is able to maintain the inside thereof in a vacuum state by operation of the vacuum pump P, and generates an electron beam under vacuum to ionize titanium (Ti) into deposition particles.

The bracket holder 320 is installed in the chamber 310, is rotated at a predetermined angle by a rotational force of the motor M, and fixes the brackets 100 to be coated.

The bracket holder 320 is rotated 360° with the brackets 100 fixed or is repetitively rotated 180° in forward and backward directions, thereby causing a Ti coating layer to be uniformly formed on each bracket 100 to a predetermined thickness.

The bracket holder 320 is connected to a negative terminal of the bias power supply 270. When bias power of the bias power supply 370 is applied for deposition, plasma is formed in the chamber 310, and evaporated Ti particles having positive polarity are deposited on the brackets 100 fixed to the bracket holder 320, thereby forming a coating layer on each bracket 100 to a predetermined thickness.

The target electrode 330 is an anode electrode, and serves as a crucible into which Ti, a coating material, is loaded. The target electrode 330 is connected with a positive terminal of the electron beam power supply 350. When power for generating an electron beam is supplied by the electron beam power supply 350, the target electrode 330 causes high current reaction with the electron gun 360 for HCD, thereby generating the electron beam resulting from glow discharge.

The heater 340 preheats the inside of the chamber 310 to a predetermined temperature in order to allow the Ti coating layer to be easily formed on the brackets 100. Here, the predetermined temperature of the inside of the chamber 310 may be detected by a typical temperature sensor and displayed on a display device (e.g. a 7-segment panel, a liquid crystal display (LCD) panel, a light-emitting diode (LED) panel, or the like) which can be observed by a worker, and is a temperature indicated on a level gauge of a temperature regulator.

The electron beam power supply 350 applies the power for generating an electron beam to the electron gun 360 for HCD and the target electrode 330, and generates the electron beam resulting from glow discharge. Here, the positive terminal of the electron beam power supply 350 is connected to the target electrode 330, and the negative terminal of the electron beam power supply 350 is connected to the electron gun 360.

The electron gun 360 includes a filament cathode, and is connected with the negative terminal of the electron beam power supply 350. When the electron beam generating power is supplied from the electron beam power supply 350, the electron gun 360 causes high current reaction with the target electrode 330, thereby generating the electron beam resulting from glow discharge.

When the electron gun 360 causes the high current reaction with the target electrode 330 to generate the electron beam, the electron beam ionizes the Ar gas in the chamber 310, and evaporates the Ti loaded into the target electrode 330 in atomic or molecular particles, so that plasma including Ar cations and evaporated Ti particles is generated. Here, the Ar cations are accelerated toward and collide with the Ti loaded on the target electrode 330, and the Ti loaded into the target electrode 330 is evaporated in atomic or molecular particles. As a result, the plasma including the Ar cations and the evaporated Ti particles is generated in the chamber 310.

The bias power supply 370 applies a voltage of 50 to 100 V of bias power for deposition to the bracket holder 320, so that the evaporated Ti particles forming the plasma in the chamber 310 are deposited on the brackets 100 fixed to the bracket holder 320, and thus form a coating layer having a predetermined thickness on each bracket.

The bias power supply 370 preferably applies the voltage of 50 to 100 V of the bias power for deposition to the bracket holder 320 at intervals of 30 to 60 seconds.

The surface coating method for an orthodontic corrective bracket is performed by the ion plating apparatus 300 configured as described above, as shown in FIGS. 3 and 4.

Figure 3:
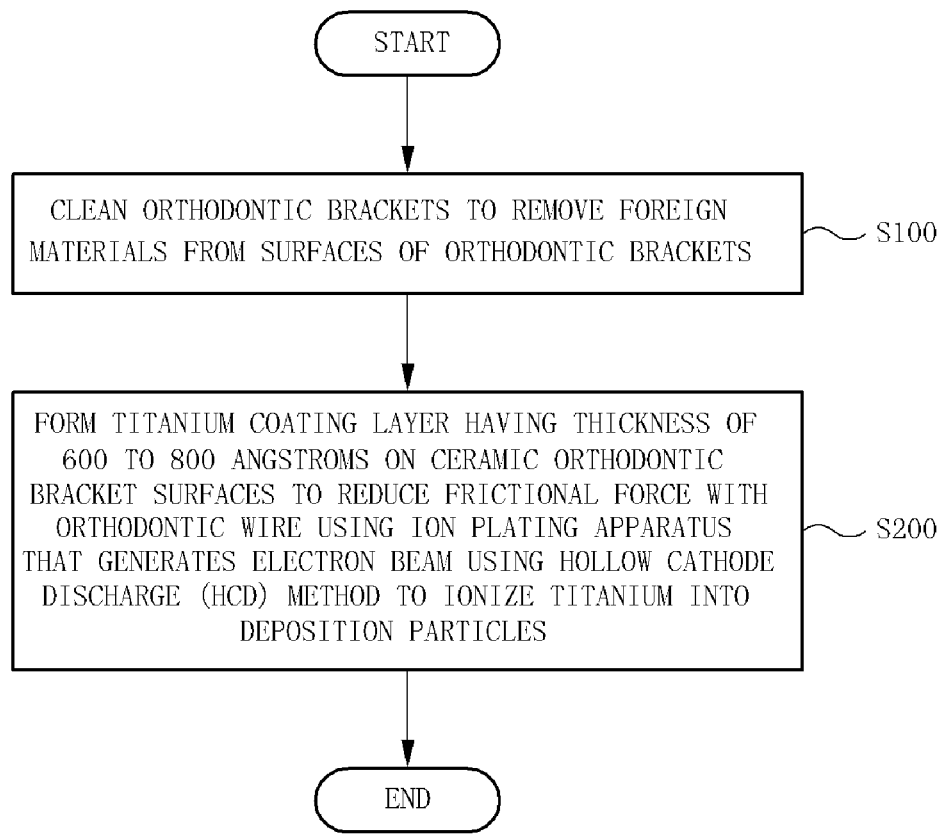
FIG. 3 is a flowchart showing a surface coating method for an orthodontic corrective bracket according to an exemplary embodiment of the present invention.

Referring to FIG. 3, a worker cleans a plurality of brackets 100 formed of a ceramic as described above, thereby removing foreign materials from surfaces of the brackets (S100).

Here, after the foreign materials are removed from the surfaces of the ceramic brackets 100 using an alkali detergent or an ultrasonic cleaner, the brackets 100 are cleaned using water, the foreign materials are finally removed from the surfaces of the brackets 100 using alcohol or acetone, and the brackets 100 are dried.

Next, the worker operates the ion plating apparatus 300, which generates an electron beam using an HCD method and ionizes Ti into deposition particles, to form a Ti coating layer having a thickness of 600 to 800 angstroms on the surfaces of the ceramic brackets 100 from which the foreign materials are removed in order to reduce a frictional force with the wire 200 (S200).

For reference, the ceramic is more sensitive to metal in terms of a change in color tone caused by heat treatment. As such, when the surface coating method for an orthodontic corrective bracket according to the present invention is applied to the ceramic brackets 100, the thickness of the Ti coating layer formed on the surface of each ceramic bracket 100 is limited to the range 600 to 800 angstroms as an optimum experience value for the purpose of minimizing the frictional force with the wire 200 while stably maintaining the color tone characteristic of the ceramic brackets 100.

The process S200 of forming the Ti coating layer having a thickness of 600 to 800 angstroms on the surfaces of the ceramic brackets 100 from which the foreign materials are removed in order to reduce a frictional force with the wire 200 will be described below in detail.

Figure 4:
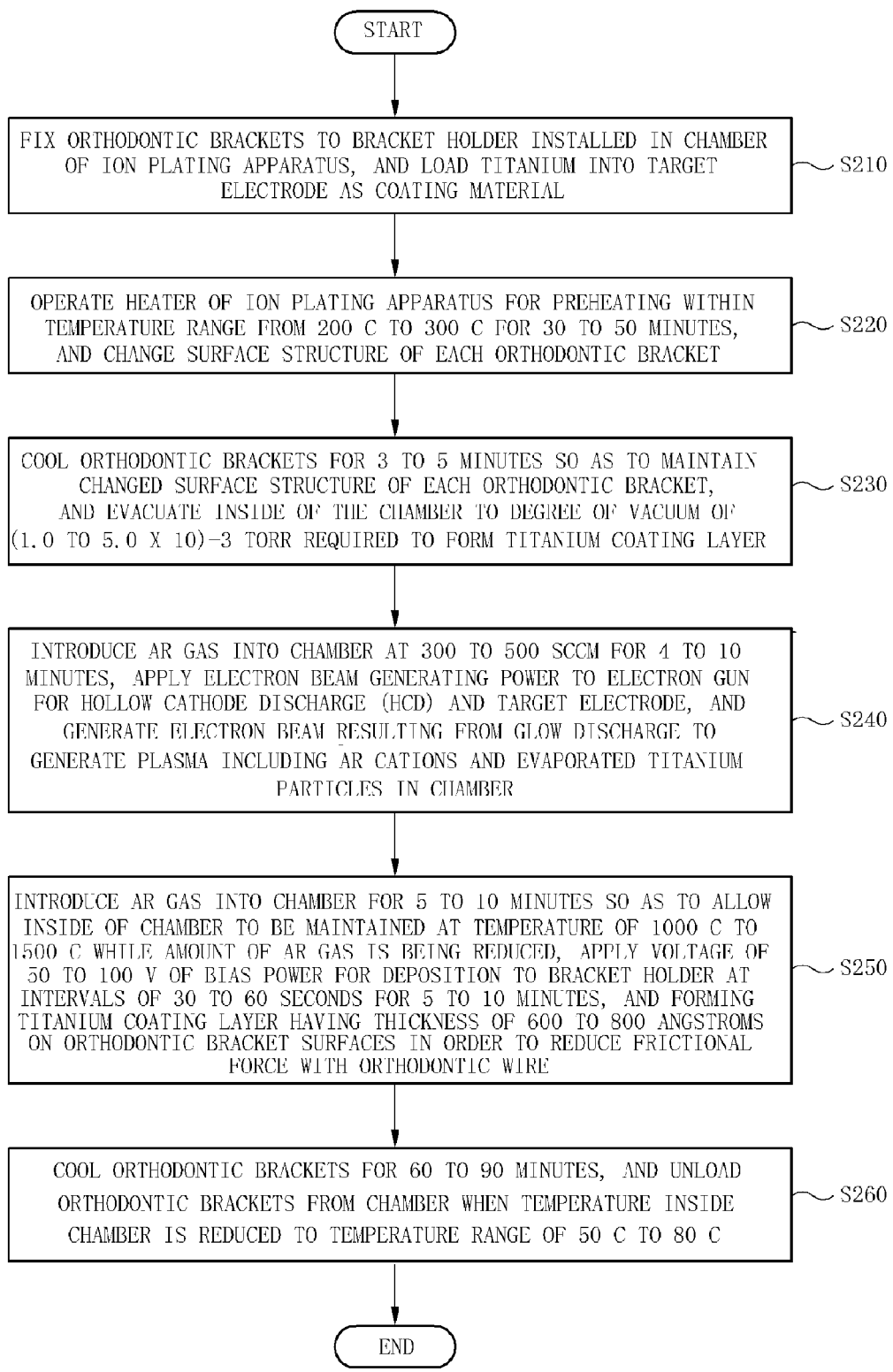
FIG. 4 is a flowchart showing the second process S200 of FIG. 3.

Referring to FIG. 4, a worker fixes a plurality of brackets 100 for coating to the bracket holder 320 installed in the chamber 310 of the ion plating apparatus 300, and then loads Ti into the target electrode 330 as a coating material (S210).

Then, the heater 340 installed in the chamber 310 of the ion plating apparatus 300 is operated for preheating within a temperature range from 200° C. to 300° C. for 30 to 50 minutes so as to allow the Ti coating layer to be readily formed on the surface of each bracket 100, and changes a surface structure of each bracket 100 loaded in the chamber 310 (S220).

For reference, the time condition (30 to 50 minutes) and the temperature condition (200° C. to 300° C.) for the preheating operation of the heater 340 are optimum conditions for forming the Ti coating layer having a thickness of 600 to 800 angstroms. Thus, if the preheating operation is beyond these conditions, adhesion strength of the Ti coating layer becomes an issue.

As described above, when the brackets 100 are preheated, the operation of the heater 340 is stopped, and the brackets 100 are cooled for 3 to 5 minutes so as to maintain the changed surface structure of each bracket 100. The vacuum pump P installed on one side of the chamber 310 is operated to evacuate the inside of the chamber 310 to a degree of vacuum of $1.0 \times 10^{-3}$ to $5.0 \times 10^{-3}$ torr required to form the Ti coating layer (S230). Here, the vacuum degree range of $1.0 \times 10^{-3}$ to $5.0 \times 10^{-3}$ torr of the inside of the chamber 310 is an optimum condition for inducing glow discharge for forming the Ti coating layer of the ceramic brackets 100. If the inside of the chamber is beyond the vacuum degree range, the glow discharge for forming the Ti coating layer of the ceramic brackets 100 may become unstable.

As described above, when the inside of the chamber 310 maintains the vacuum degree required to form the Ti coating layer, Ar gas is introduced into the chamber 310 via a plurality of gas inlets 311 formed on one side of the chamber 310 at 300 to 500 standard cubic centimeters per minute (sccm) for 4 to 10 minutes. The power for generating the electron beam is supplied to the electron gun 360 for HCD and the target electrode 330 by the electron beam power supply 350, and the electron beam resulting from glow discharge is generated, thereby ionizing the Ar gas and evaporating Ti loaded on the target electrode 330 into atomic or molecular particles. Thus, plasma including Ar cations and evaporated Ti particles is generated in the chamber 310 (S240).

In the state where the plasma is generated in the chamber 310, the Ar gas is introduced into the chamber 310 for 5 to 10 minutes so as to be able to maintain the inside of the chamber 310 at a temperature of 1000° C. to 1500° C. while an amount of the Ar gas is being reduced, thereby evaporating Ti into atomic or molecular particles. At the same time, the bias power supply 370 applies a voltage of 50 to 100 V of bias power for deposition to the bracket holder 320 at intervals of 30 to 60 seconds for 5 to 10 minutes, thereby forming a Ti coating layer having a thickness of 600 to 800 angstroms on the surfaces of the brackets 100 in order to reduce a frictional force with the wire 200 (S250).

At this time, the temperature of the inside of the chamber 310 may be detected by a typical temperature sensor and displayed on a display device (e.g. a 7-segment panel, an LCD panel, an LED panel, or the like) which can be observed by a worker.

If the temperature of the inside of the chamber 310 is higher than 1500° C., an amount of evaporated Ti is too much to maintain a color tone characteristic of the ceramic brackets 100 when the coating layer is completely formed and to ensure smooth sliding of the wire 200. If the temperature of the inside of the chamber 310 is lower than 1000° C., the amount of evaporated Ti is too little to form the coating layer to a sufficient thickness.

Further, if the voltage of the bias power for deposition applied by the bias power supply 370 is higher than 100 V, small evaporated Ti particles are mainly deposited to form the coating layer on the surface of each ceramic bracket 100, and thus the wire 200 cannot slide smoothly. If the voltage of the bias power for deposition is lower than 50 V, large evaporated Ti particles are mainly deposited to form the coating layer on the surface of each ceramic bracket 100, and thus the wire 200 slides too smoothly. In the embodiment of the present invention, to minimize the frictional force with the wire 200 while stably maintaining the color tone characteristic of the ceramic brackets 100, the voltage of the bias power for deposition applied by the bias power supply 370 is limited to the range of 50 to 100 V as an optimum experience value, and is applied to the bracket holder 320 at intervals of 30 to 60 seconds.

When the formation of the coating layer is completed, the electron beam generating power and the bias power are shut off, and the brackets 100 are cooled for 60 to 90 minutes. When the temperature of the inside of the chamber 310 is reduced to a temperature range of 50° C. to 80° C., the brackets 100 are unloaded from the chamber 310. Thereby, the coating operation is terminated (S260).

For reference, the cooling time is set to a long time of 60 to 90 minutes to prevent damage to the color tone characteristic of the brackets 100 formed of ceramic, which is relatively sensitive to the color tone change caused by heat compared to metal.

According to the present invention, when the teeth are corrected using the ceramic orthodontic brackets on whose surfaces the titanium coating layer having a predetermined thickness is formed, the frictional force can be minimized while the wire fitted into the slots of the brackets is applying the orthodontic tension to the teeth, and thus it is possible to realize a tooth movement path desired by an orthodontist and to shorten a treatment period.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A surface coating method for orthodontic brackets that are formed of ceramic by grinding, sintering, injection molding, or pressing and are each configured so that a back face thereof serves as an attachment face that is directly attached to a tooth, whereas an external face thereof on an opposite side of the back face is provided with a slot into which an orthodontic wire interconnecting the orthodontic brackets is fitted, the method comprising:

a first process of cleaning the orthodontic brackets to remove foreign materials from surfaces of the orthodontic brackets; and a second process of forming a titanium coating layer having a thickness of 600 to 800 angstroms on the surfaces of the orthodontic brackets from which the foreign materials are removed, to reduce frictional force with the orthodontic wire using an ion plating apparatus that generates an electron beam using a hollow cathode discharge (HCD) method to ionize titanium into deposition particles, the second process including a first sub-process of fixing a plurality of the orthodontic brackets for coating to a bracket holder that is installed in a chamber of the ion plating apparatus, receives a rotational force from a motor, and rotates at a predetermined angle, and loading titanium into a target electrode as a coating material, a second sub-process of operating a heater, which is installed in the chamber of the ion plating apparatus, for preheating within a temperature range from 200° C. to 300° C. for 30 to 50 minutes so that the titanium coating layer is readily formed on the surface of each orthodontic bracket, and changing a surface structure of each orthodontic bracket loaded in the chamber, a third sub-process of stopping the operation of the heater when the orthodontic brackets are preheated, cooling the orthodontic brackets for 3 to 5 minutes so as to maintain the changed surface structure of each orthodontic bracket, and operating a vacuum pump, which is installed on one side of the chamber to evacuate the inside of the chamber to a degree of vacuum of $1.0 \times 10^{-3}$ to $5.0 \times 10^{-3}$ torr required to form the titanium coating layer, a fourth sub-process of, when the inside of the chamber maintains the vacuum degree required to form the titanium coating layer, introducing argon gas into the chamber via a plurality of gas inlets formed on one side of the chamber at 300 to 500 sccm for 4 to 10 minutes, applying power for generating the electron beam from an electron beam power supply to an electron gun for the HCD and the target electrode, generating the electron beam resulting from glow discharge to ionize the argon gas and to evaporate the titanium loaded on the target electrode into atomic or molecular particles, and generating plasma including argon cations and evaporated titanium particles in the chamber, a fifth sub-process of, in a state where the plasma is generated in the chamber, introducing the argon gas into the chamber for 5 to 10 minutes so that the inside of the chamber is maintained at a temperature of 1000° C. to 1500° C. while an amount of the argon gas is being reduced, evaporating the titanium into the atomic or molecular particles, applying a voltage of 50 to 100 V of bias power for deposition from a bias power supply to the bracket holder at intervals of 30 to 60 seconds for 5 to 10 minutes, and forming the titanium coating layer having a thickness of 600 to 800 angstroms on the surfaces of the orthodontic brackets in order to reduce the frictional force with the orthodontic wire, and a sixth sub-process of, when the formation of the coating layer is completed, shutting off the electron beam generating power and the bias power, cooling the orthodontic brackets for 60 to 90 minutes, and unloading the orthodontic brackets from the chamber to terminate the coating operation when the temperature of the inside of the chamber is reduced to a temperature range of 50° C. to 80° C.

2. The method of claim 1, wherein the first process includes
a first removing process to remove the foreign materials from the surfaces of the orthodontic brackets by using an alkali detergent or an ultrasonic cleaner,
cleaning the orthodontic brackets using water,
a second removing process to remove the foreign materials from the surfaces of the orthodontic brackets by using alcohol or acetone, and
drying the orthodontic brackets.

* * * * *